(12) United States Patent
Puccio et al.

(10) Patent No.: US 9,066,966 B2
(45) Date of Patent: Jun. 30, 2015

(54) METHODS AND PHARMACEUTICAL COMPOSITIONS FOR THE TREATMENT OF CARDIOMYOPATHY DUE TO FRIEDREICH ATAXIA

(71) Applicants: Institut National de la Sante et de la Recherche Medicale (INSERM), Paris (FR); CNRS (Centre National de la Recherche Scientifique), Paris (FR); Universite de Strasbourg, Strasbourg (FR); Cornell University, Ithaca, NY (US); Universite Paris-Sud XI, Orsay Cedex (FR); Assistance Publique-Hopitaux de Paris (APHP), Paris (FR)

(72) Inventors: Helene Monique Puccio, Illkirch (FR); Patrick Aubourg, Le Kremlin Bicetre (FR); Ronald G. Crystal, New York, NY (US); Pierre Bougneres, Le Kremlin Bicetre (FR)

(73) Assignees: Institut National de la Sante et de la Recherche Medicale (INSERM), Paris (FR); CNRS (Centre National de la Recherche Scientifique), Paris (FR); Universite de Strasbourg, Strasbourg (FR); Cornell University, Itahca, NY (US); Universite Paris-Sud XI, Orsay Cedex (FR); Assistance Publique-Hopitaux de Paris (APHP), Paris (FR)

(*) Notice: Subject to any disclaimer, the term of this patent is extended or adjusted under 35 U.S.C. 154(b) by 0 days.

(21) Appl. No.: 13/756,651

(22) Filed: Feb. 1, 2013

(65) Prior Publication Data
US 2014/0221462 A1 Aug. 7, 2014

(51) Int. Cl.
*A61K 48/00* (2006.01)
*A61K 31/713* (2006.01)
*A61P 9/00* (2006.01)
*C12N 15/864* (2006.01)
*A61K 31/7088* (2006.01)
*C07K 14/47* (2006.01)

(52) U.S. Cl.
CPC .............. *A61K 31/7088* (2013.01); *A61K 48/00* (2013.01); *A61K 48/0016* (2013.01); *A61K 48/005* (2013.01); *C07K 14/47* (2013.01); *C12N 2750/14032* (2013.01); *C12N 2750/14071* (2013.01)

(58) Field of Classification Search
CPC .............. A61K 48/00; A61K 48/0075; A61K 38/1709; C12N 15/11; C12N 15/8645; C12N 5/06; C12N 2750/14032
See application file for complete search history.

(56) References Cited

U.S. PATENT DOCUMENTS

2014/0135275 A1* 5/2014 Keefe et al. .................. 514/21.2

OTHER PUBLICATIONS

Daya and Berns, Gene Therapy Using Adeno-Associated Virus Vectors, Clinical Microbiology Reviews, Oct. 2008, p. 583-593.*
Hu et al RH10 provides superior transgene expression in mice when compared with natural AAV serotypes for neonatal gene therapy, J Gene Med. Sep. 2010; 12(9): 766-778.*
Lim et al, Functional Recovery in a Friedreich's Ataxia Mouse Model by Frataxin Gene Transfer Using an HSV-1 Amplicon Vector, Molecular Therapy vol. 15 No. 6 Jun. 2007, pp. 1072-1078.*
Ristow et al, Frataxin activates mitochondrial energy conversion and oxidative phosphorylation, PNAS, Oct. 24, 2000 u vol. 97, pp. 12239-12243.*
Chu et al, "Gene Delivery to the Mammalian Heart Using AAV Vectors" from Methods in Molecular Biology, vol. 246: Gene Delivery to Mammalian Cells: vol. 2: Viral Gene Transfer Techniques, 2004 pp. 213-224.*
Puccio et al, Mouse models for Friedreich ataxia exhibit cardiomyopathy, sensory nerve defect and Fe—S enzyme deficiency followed by intramitochondrial iron deposits, Nature Genetics, 2001, pp. 181-186.*
Melo et al, Gene and cell-based therapies for heart disease, Molecular Therapies for Heart Disease, 2004 pp. 648-663.*

* cited by examiner

*Primary Examiner* — Maria Marvich
(74) *Attorney, Agent, or Firm* — Whitham, Curtis, Christofferson & Cook, P.C.

(57) ABSTRACT

A method for preventing or treating cardiomyopathy due to energy failure in a subject in need thereof is provided. The method comprises administering to the subject a therapeutically effective amount of a vector which comprises a nucleic acid sequence encoding a gene that can reverse energy failure. An exemplary cardiomyopathy is that which is associated with Friedreich ataxia and an exemplary nucleic acid sequence comprises a nucleic acid that encodes frataxin (FXN).

21 Claims, 6 Drawing Sheets

Figure 1:
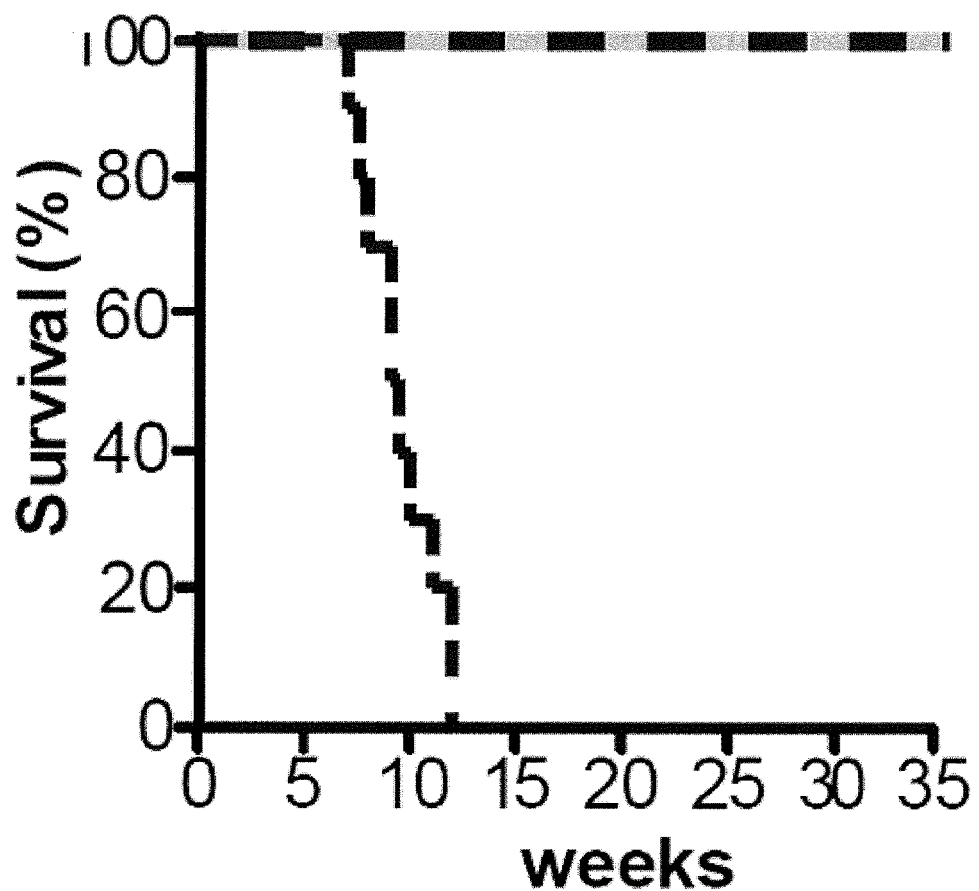

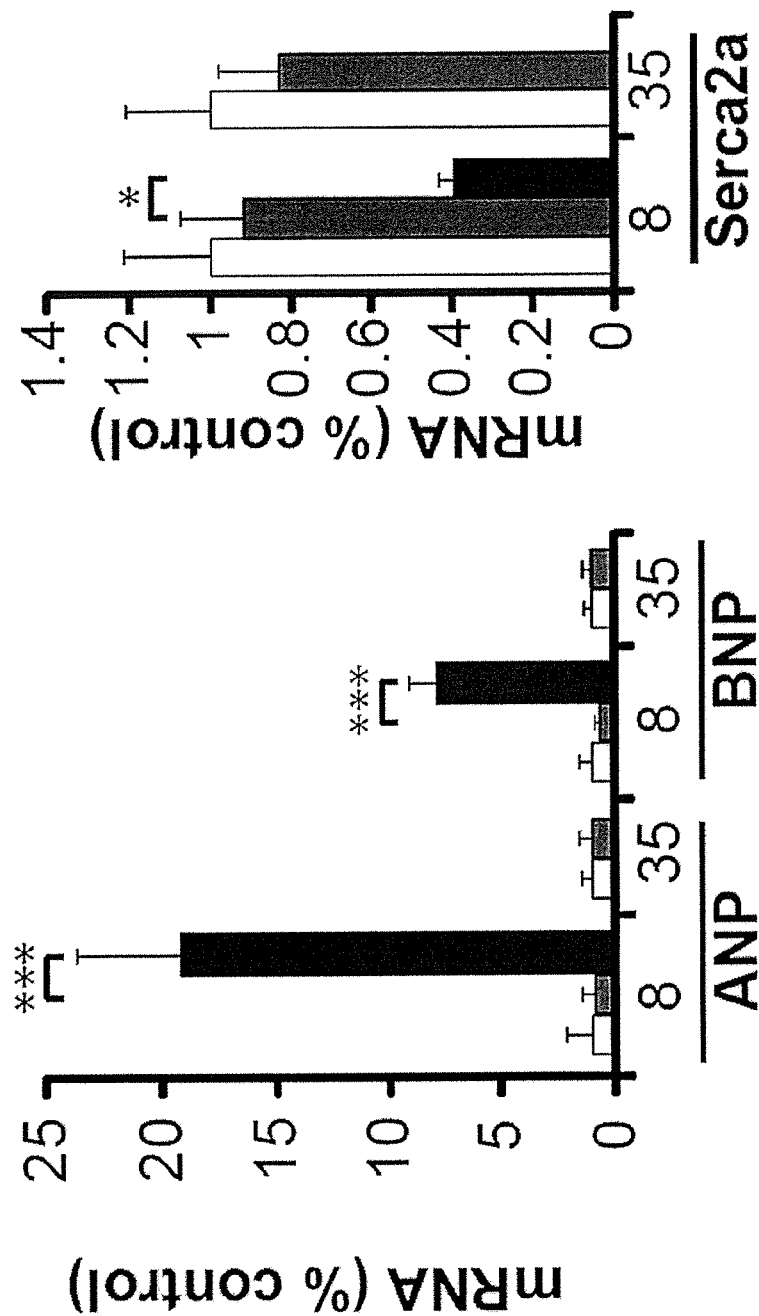
Figure 1 B2
Figure 1 B1

Figure 2:
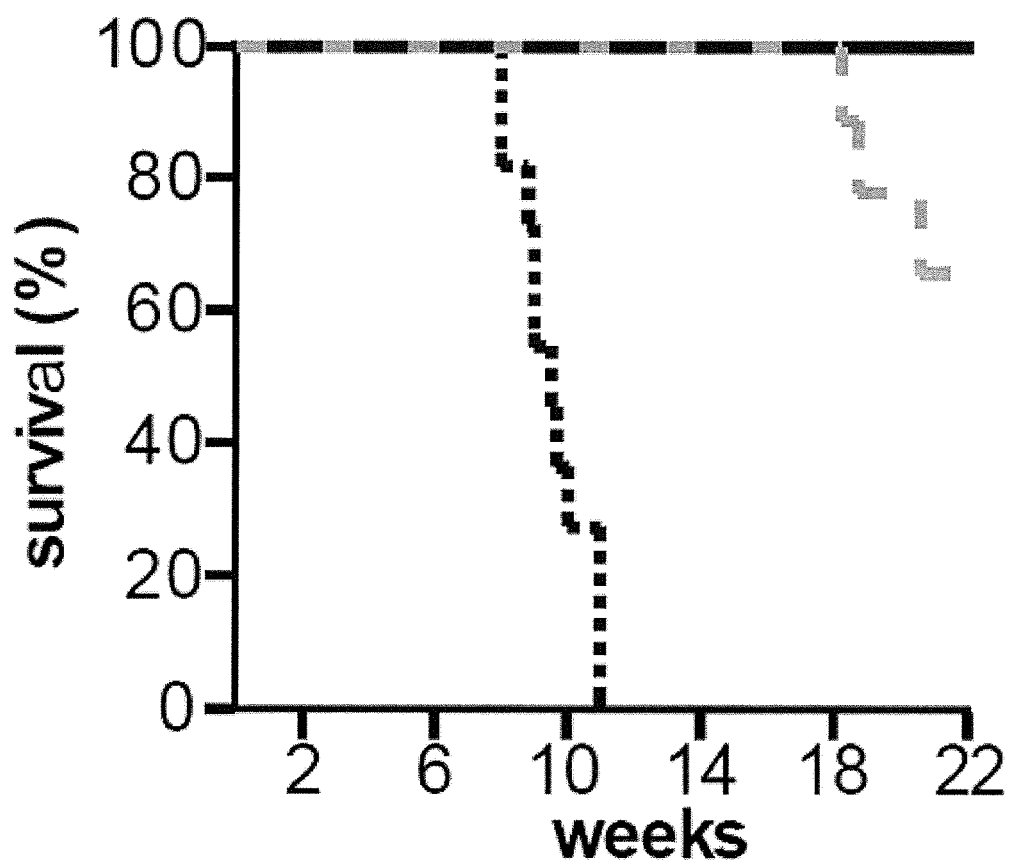
Figure 2:
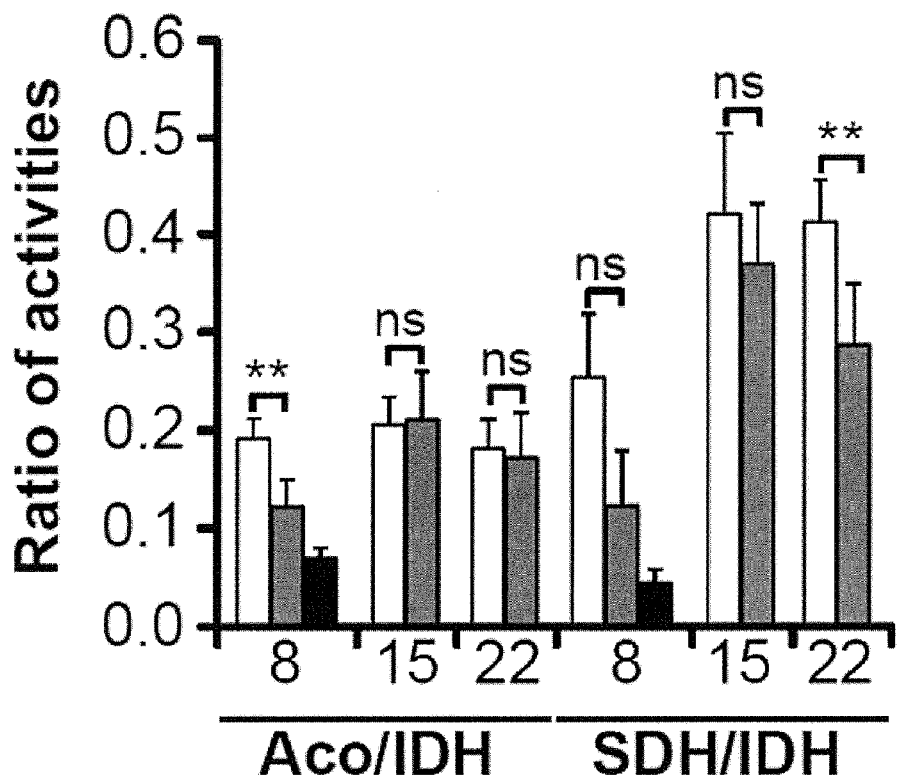

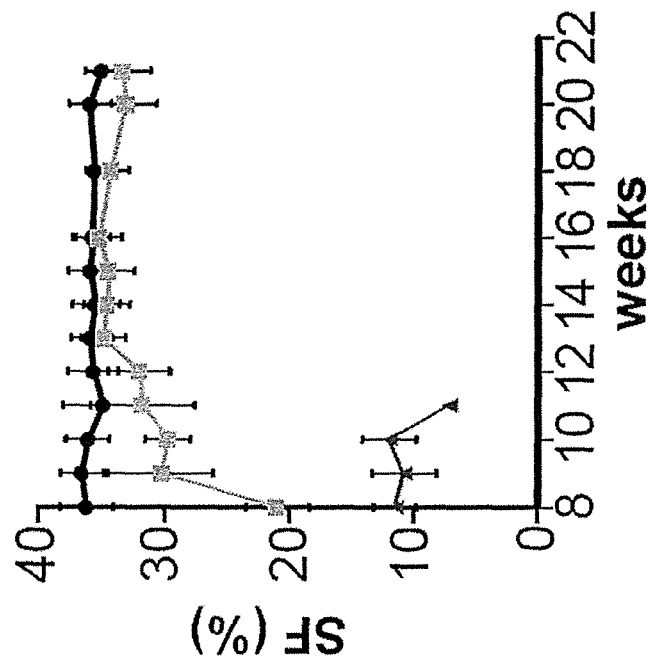
Figure 2 A2
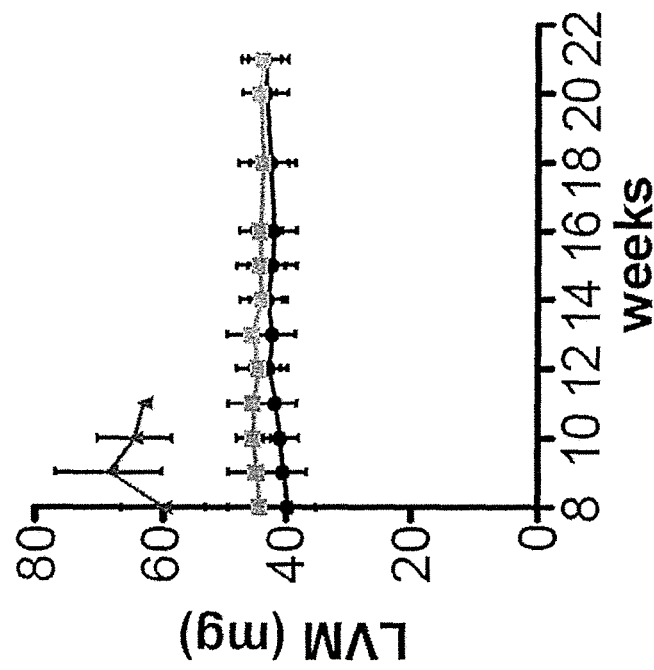
Figure 2 A1

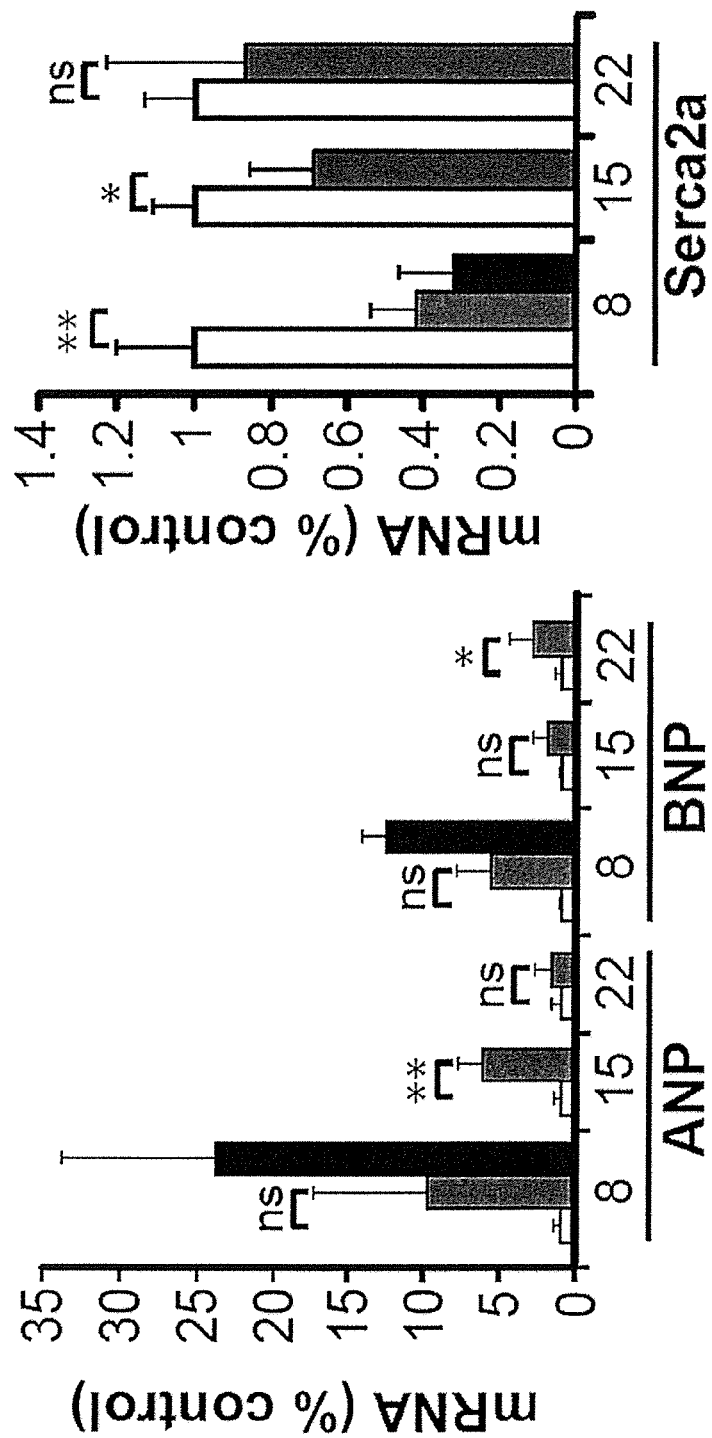
Figure 2 C2
Figure 2 C1

SEQUENCE LISTING

```
<160> NUMBER OF SEQ ID NOS: 2

<210> SEQ ID NO 1
<211> LENGTH: 7168
<212> TYPE: DNA
<213> ORGANISM: Homo sapiens

<400> SEQUENCE: 1
agtctccctt gggtcagggg tcctggttgc actccgtgct ttgcacaaag caggctctcc      60
atttttgtta aatgcacgaa tagtgctaag ctgggaagtt cttcctgagg tctaacctct     120
agctgctccc ccacagaaga gtgcctgcgg ccagtggcca ccaggggtcg ccgcagcacc     180
cagcgctgga gggcggagcg ggcggcagac ccggagcagc atgtggactc tcgggcgccg     240
cgcagtagcc ggcctcctgg cgtcacccag cccagcccag gccagaccc  tcacccgggt     300
```

```
cccgcggccg gcagagttgg ccccactctg cggccgccgt ggcctgcgca ccgacatcga    360
tgcgacctgc acgccccgcc gcgcaagttc gaaccaacgt ggcctcaacc agatttggaa    420
tgtcaaaaag cagagtgtct atttgatgaa tttgaggaaa tctggaactt tgggccaccc    480
aggctctcta gatgagacca cctatgaaag actagcagag gaaacgctgg actctttagc    540
agagtttttt gaagaccttg cagacaagcc atacacgttt gaggactatg atgtctcctt    600
tgggagtggt gtcttaactg tcaaactggg tggagatcta ggaacctatg tgatcaacaa    660
gcagacgcca aacaagcaaa tctggctatc ttctccatcc agtggaccta agcgttatga    720
ctggactggg aaaaactggg tgtactccca cgacggcgtg tccctccatg agctgctggc    780
cgcagagctc actaaagcct aaaaaccaaa ctggacttgt cttccttggg cctattccgg    840
aaaagatgct tgatgcccag ccccgtttta aggacattaa aagctatcag gccaagaccc    900
cagcttcatt atgcagctga ggtctgtttt ttgttgttgt tgttgtttat tttttttatt    960
cctgcttttg aggacagttg ggctatgtgt cacagtctg tagaaagaat gtgttgcctc    1020
ctaccttgcc cccaagttct gattttttaat ttctatggaa gatttttttgg attgtcggat  1080
ttcctccctc acatgatacc ccttatcttt tataatgtct tatgcctata cctgaatata   1140
acaacccttta aaaagcaaaa ataataagaa ggaaaaattc caggagggaa aatgaattgt   1200
cttcactctt cattctttga aggatttact gcaagaagta catgaagagc agctggtcaa   1260
cctgctcact gttctatctc caaatgagac acattaaagg gtagcctaca aatgttttca   1320
ggcttctttc aaagtgtaag cacttctgag ctctttagca ttgaagtgtc gaaagcaact   1380
cacacgggaa gatcatttct tatttgtgct ctgtgactgc caaggtgtgg cctgcactgg   1440
gttgtccagg gagacctagt gctgtttctc ccacatattc acatacgtgt ctgtgtgtat   1500
atatattttt tcaatttaaa ggttagtatg gaatcagctg ctacaagaat gcaaaaaatc   1560
ttccaaagac aagaaagag gaaaaaaagc cgttttcatg agctgagtga tgtagcgtaa    1620
caaacaaaat catggagctg aggaggtgcc ttgtaaacat gaaggggcag ataaaggaag   1680
gagatactca tgttgataaa gagagccctg gtcctagaca tagttcagcc acaaagtagt   1740
tgtcccttttg tggacaagtt tcccaaattc cctggacctc tgcttcccca tctgttaaat  1800
gagagaatag agtatggttg attcccagca ttcagtggtc ctgtcaagca acctaacagg   1860
ctagttctaa ttcccctattg ggtagatgag gggatgacaa agaacagttt ttaagctata  1920
taggaaacat tgttattggt gttgccctat cgtgatttca gttgaattca tgtgaaaata   1980
atagccatcc ttggcctggc gcggtggctc acacctgtaa tcccagcact tttgaggcc    2040
aaggtgggtg gatcacctga ggtcaggagt tcaagaccag cctggccaac atgatgaaac   2100
cccgtctcta ctaaaaatac aaaaaattag ccgggcatga tggcaggtgc ctgtaatccc   2160
agctacttgg gaggctgaag cggaagaatc gcttgaaccc agaggtggag gttgcagtga   2220
gccgagatcg tgccattgca ctgtaacctg ggtgactgag caaaactctg tctcaaaata   2280
ataataacaa tataataata ataatagcca tcctttattg tacccttact gggttaatcg   2340
tattatacca cattacctca tttttaatttt tactgacctg cactttatac aaagcaacaa   2400
gcctccagga cattaaaatt catgcaaagt tatgctcatg ttatattatt tcttactta    2460
aagaaggatt tattagtggc tgggcatggt ggcgtgcacc tgtaatccca ggtactcagg   2520
aggctgagac gggagaattg cttgacccca ggcggaggag gttacagtga gtcgagatcg   2580
tacctgagcg acagagcgag actccgtctc aaaaaaaaaa aaaggagggg tttattaatg   2640
```

```
agaagtttgt attaatatgt agcaaaggct tttccaatgg gtgaataaaa acacattcca    2700
ttaagtcaag ctgggagcag tggcatatac ctatagtccc agctgcacag gaggctgaga    2760
caggaggatt gcttgaagcc aggaattgga gatcagcctg gcaacacag caagatccta     2820 tctcttaaaa aaagaaaaaa aaacctatta ataataaaac agtataaaca aaagctaaat    2880
aggtaaaata ttttttctga aataaaatta ttttttgagt ctgatggaaa tgtttaagtg    2940
cagtaggcca gtgccagtga gaaaataaat aacatcatac atgtttgtat gtgtttgcat    3000
cttgcttcta ctgaaagttt cagtgcaccc cacttactta gaactcggtg acatgatgta    3060
ctcctttatc tgggacacag cacaaaagag gtatgcagtg gggctgctct gacatgaaag    3120
tggaagttaa ggaatctggg ctcttatggg gtccttgtgg gccagccctt caggcctatt    3180
ttactttcat tttacatata gctctaattg gtttgattat ctcgttccca aggcagtggg    3240
agatccccat ttaaggaaag aaaaggggcc tggcacagtg gctcatgcct gtaatcccag    3300
cactttggga ggctgaggca gtgtatcac ctgaggtcag gagttcaaga ccagcctggc     3360
caacatggca aaatcccgtc tctactaaaa atattaaaaa attggctggg cgtggtggtt    3420
cgtgcctata atttcagcta ctcaggaggc tgaggcagga gaatcgctgt aacctggggg    3480
gtggaggttg cagtgagacg agatcatgcc acttcactcc agcctggcca acagagccat    3540
actccgtctc aaataaataa ataaataaat aaagggactt caaacacatg aacagcagcc    3600
aggggaagaa tcaaaatcat attctgtcaa gcaaactgga aaagtaccac tgtgtgtacc    3660
aatagcctcc ccaccacaga ccctgggagc atcgcctcat ttatggtgtg gtccagtcat    3720
ccatgtgaag gatgagtttc caggaaaagg ttattaaata ttcactgtaa catactggag    3780
gaggtgagga attgcataat acaatcttag aaaacttttt ttttcccttt ctattttttg    3840
agacaggatc tcactttggc actcaggctg gaggacagtg gtacaatcaa agctcatggc    3900
agcctcgacc tccctgggct tgggcaatcc tcccacaggt gtgcacctcc atagctggct    3960
aatttgtgta ttttttgtag agatgggggtt tcaccatgtt gcccaggctg gtctctaaca   4020
cttaggctca agtgatccac ctgcctcgtc ctcccaagat gctgggatta caggtgtgtg    4080
ccacaggtgt tcatcagaaa gcttttttcta ttatttttac cttcttgagt gggtagaacc    4140
tcagccacat agaaaataaa atgttctggc atgacttatt tagctctctg gaattacaaa    4200
gaaggaatga ggtgtgtaaa agagaacctg ggtttttgaa tcacaaattt agaatttaat    4260
cgaaactctg cctcttactt gtttgtagac actgacagtg gcctcatgtt tttttttttt    4320
ttaatctata aaatggagat atctaacatg ttgagcctgg gcccacaggc aaagcacaat    4380
cctgatgtga gaagtactca gttcatgaca actgttgttc tcacatgcat agcataattt    4440
catattcaca ttggaggact tctcccaaaa tatggatgac gttccctact caaccttgaa    4500
cttaatcaaa atactcagtt tacttaactt cgtattagat tctgattccc tggaaccatt    4560
tatcgtgtgc cttaccatgc ttatatttta cttgatcttt tgcataccttt ctaaaactat    4620 tttagccaat ttaaaatttg acagtttgca ttaaattata ggtttacaat atgctttatc    4680
cagctatacc tgccccaaat tctgacagat gcttttgcca cctctaaagg aagacccatg    4740
ttcatagtga tggagtttgt gtggactaac catgcaaggt tgccaaggaa aaatcgcttt    4800
acgcttccaa ggtacacact aagatgaaag taattttagt ccgtgtccag ttggattctt    4860
ggcacatagt tatcttctgc tagaacaaac taaaacagct acatgccagc aagggagaaa    4920
ggggaaggag gggcaaagtt ttgaaatttc atgtaaattt atgctgttca aaacgacgag    4980
ttcatgactt tgtgtataga gtaagaaatg cctttttcttt tttgagacag agtcttgctc    5040
```

```
tgtcacccag gctggagtgc agtggcacga tctgggctca ctacaacctc cgcctcctgg    5100
gttcaagcaa ttctctgcct cagcctcccg agtagctggg attacaggtg cctgccacca    5160
cacccggcta ttttttgtat ttttagtaga cacggggttt caccatcatg gccaggctgg    5220
tcttgaactc ctgacctagt aatccacctg cctccgcctc ccaaagtgct gggattacag    5280
gcgtgagcca ctgcacccag ccagaaatgc cttctaatct ttggtttatc ttaattagcc    5340
aggacacttg gagtgcatcc cgaagtacct gatcagtggc ccctttggaa tgtgtaaaac    5400
tcagctcact tatatccctg catccgctac agagacagaa tccaagctca tatgttccat    5460
cttctctggc tgtatagttt aaggaatgga aggcaccaga acagatttat tgaaatgttt    5520
attagctgaa gatttattta gacagttgag gaaaacatca gcacccagca gtaaaattgg    5580
ctctcaaaga ttttcttctc ctgtggaaag tcagacctct gaggccccat ccaggtagaa    5640
gtactagtgc aagaagggcc tctgctgtcc acttgtgttt ctgtgatctg tgggaacatt    5700
gttaacgcca catcttgacc tcaaattgtt tagctcctgg ccagacacgg tggctcacac    5760
ctgtaatccc agcactttga gaggctgagg caggtggatc acctgaggtt aggagttcga    5820
ggccagcctg gtcaacatgg taaaaccccg cctctactaa aaatacaaaa attagctggc    5880
cgtagtggcg cacgcctgtt atcccagcta ctcgggaggc tgaggcagga gaattgcttg    5940
aacctgggtg gtggaggttg cagtgagccg agattacacc actgcactcc agcctgggtg    6000
acaagaggga aactccatta aaaaaatgta attcccgtgt ctgccatctt aagtgtaaag    6060
gtggctaaat tatatagaaa aataagacaa tatcatttcc caattacatt cctttcctac    6120
cgcactctat gatgctagct gagatttttc caaaagaaaa tggcttaaat aaaaccctaa    6180
gagaaagaaa aactttaaat ccctccaaag ctcaaaagta atagaaacag atgagtttgg    6240
agtcaggatt tctctgtaag attgcctagg ctgtgtactg cacatctcca ggtgccactg    6300
ttgacagaga ttataactac aatgtgaagt gaatggtgcc actgacagtt atgcaaaccg    6360
tccagagcat agccacctga tcctgctggg attcctcttg ccagtccatc agcagttccc    6420
cttgaaagtt tcaccaaaca tcccttaaat ctgccctctc ctgcccgtcc ccagtggagg    6480
tcctcatcat ttttcacctg cattttttgca ggagctttct tatatccacc ttcctccttt    6540
tctctcagcc catcatctag ctacacagtc tccagggtaa gctttcagaa aggcaatctc    6600
ttgtctgtaa aacctaagca ggaccaaggc caagtttctt agcctgaaaa atgtgctttt    6660
ctgactgaac tgttcaggca ctgactctac atataattat gctttttctac cccctcacac    6720 tcaacacttt gactccagca atcccaaatc cccagatccc taagtgtgct gtgctatttt    6780
cacgtggctc tcagacttgg ccagtgctgt ttccattttg gtctttattc cccacatctc    6840
tgcctggggg gtagattcta ccctgaaaaa tgttcttggc acagccttgc aaactcctcc    6900
tccactcagc ctctgcctgg atgcccttga ttgttccatg tcctcagcat accatgtttg    6960
tctttcccag cactgaccta ccatgtgtca ccctgcttg gctgtacctt ccatgaggct    7020
aggactatgt gtctcctttg ttgactgctg ttgccctagc atcttgcaca gttccttgca    7080
cacaattaga gctctataaa tgtcaaataa atgtgttata attatatgtt taagatagtt    7140
gttcaaataa actctaaata accccaac                                        7168
```

<210> SEQ ID NO 2
<211> LENGTH: 210
<212> TYPE: PRT
<213> ORGANISM: Homo sapiens

```
<400> SEQUENCE: 2

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
            195                 200                 205

Asp Ala
    210
```

METHODS AND PHARMACEUTICAL COMPOSITIONS FOR THE TREATMENT OF CARDIOMYOPATHY DUE TO FRIEDREICH ATAXIA

FIELD OF THE INVENTION

The present invention relates a method for preventing or treating cardiomyopathy due to energy failure in a subject in need thereof, comprising administering to said subject a therapeutically effective amount of a vector which comprises a nucleic acid sequence of a gene that can reverse energy failure.

More particularly, the invention relates to a method for preventing or treating a cardiomyopathy associated with Friedreich ataxia in a subject in need thereof, comprising administering to said subject a therapeutically effective amount of a vector which comprises a frataxin (FXN) encoding nucleic acid.

BACKGROUND OF THE INVENTION

Friedreich ataxia (FRDA), an autosomal progressive recessive neurodegenerative disorder associated with cardiomyopathy, is caused by reduced expression of the mitochondrial protein, frataxin [V. Campuzano et al., 1996 and V. Campuzano et al., 1997]. The cardiomopathy associated with FRDA is hypertrophic. As the disease progresses, there is a natural transition from hypertrophy to dilation, with death of cardiomyocytes replaced by fibrotic tissue leading to systolic and diastolic dysfunction [R. M. Payne et al., 2012]. Impaired myocardial perfusion reserve index associated with microvascular dysfunction and fibrosis occurs even prior to the onset of overt cardiomyopathy. Consistent with impaired mitochondrial respiratory chain function that leads to energy deficit, phosphorus magnetic resonance spectroscopy shows reduced ATP production in patient heart, which strongly correlates with the degree of cardiac hypertrophy. Cardiac dysfunction, predisposing to congestive heart failure and supraventricular arrhythmias, is the primary mode of death in ~60% of patients with FRDA.

Although the function of frataxin is still under investigation, available evidence supports a role as an activator of iron-sulfur (Fe—S) cluster biogenesis in mitochondria [C. L. Tsai et al., 2010 and Schmucker et al., 2012]. In particular, frataxin was recently shown to control iron delivery for de novo Fe—S cluster biogenesis through activation of cysteine desulfurase activity [Colin et al., 2013].

Fe—S clusters are essential prosthetic groups for many proteins with a variety of functions and subcellular localizations. Frataxin deficiency leads to impairment of Fe—S cluster-containing proteins, altered cellular iron metabolism, mitochondrial dysfunction and increased sensitivity to oxidative stress. Most mitochondrial and biochemical defects identified in human patients have been recapitulated in mouse models of FRDA [H. Puccio et al., 2001 and Simon et al. et al., 2004], providing valuable models for testing potential therapeutic interventions. Particularly, the MCK conditional mouse model, with complete frataxin deletion in cardiac and skeletal muscle, recapitulates the cardiomyopathy observed in FRDA patients with a more rapidly progressive course [H. Puccio et al., 2001 and H. Seznec et al., 2004]. Furthermore, the MCK mouse demonstrated that hypertrophy and mitochondrial Fe—S cluster protein defects precede mitochondrial iron accumulation and increase sensitivity to oxidative stress.

To date, no treatment exists for stopping or slowing down the cardiomyopathy of FRDA. Current therapeutic approaches in clinical use or under evaluation are directed at alleviating symptoms and maximizing quality of life [R. B. Wilson 2012]. Thus, there is an important need for a novel therapeutic approach to treat cardiomyopathy associated with Friedreich ataxia.

SUMMARY OF THE INVENTION

In the present invention, the therapeutic effect of an AVVrh10 vector carrying a human frataxin cDNA on the cardiac phenotype in a mammalian model of FRDA cardiomyopathy was investigated. The results showed that delivery of a vector encoding hFXN resulted in i) prevention of the development of disease symptoms in asymptomatic individuals and ii) reversal of disease symptoms in individuals who already exhibited cardiomyopathy, mitochondrial dysfunction and the biochemical impairment associated with frataxin deficiency.

More generally, the inventors show that by restoring an essential mitochondrial function with the use of the nuclear-encoded FXN gene, and thereby increasing the energy production of the mitochondria, the myocardium function can be restored and the interstitial cardiac fibrosis stopped. Considering that inefficient energy utilization and increased energy demand by the sarcomere have been suggested as a key consequence of many, if not all, hypertrophic cardiomyopathy associated mutations (Sweeney H L et al., 1998), the results demonstrate that the use of a gene that can reverse energy failure is useful for preventing or treating cardiomyopathy linked to or associated with energy failure.

Thus, the invention relates to a method for preventing or treating cardiomyopathy due to energy failure in a subject in need thereof, comprising administering to said subject a therapeutically effective amount of a vector which comprises a nucleic acid sequence of a gene that can reverse energy failure.

More particularly, the invention relates to a method for preventing or treating a cardiomyopathy associated with Friedreich ataxia in a subject in need thereof, comprising administering to said subject a therapeutically effective amount of a vector which comprises a frataxin (FXN) encoding nucleic acid.

DETAILED DESCRIPTION OF THE INVENTION

Methods of the Invention

A first object of the invention relates to a method for preventing or treating cardiomyopathy due to energy failure in a subject in need thereof, comprising administering to said subject a therapeutically effective amount of a vector which comprises a nucleic acid sequence of a gene that can reverse energy failure.

By "energy failure" we mean inadequate or abnormal energy production by mitochondria, and/or lower than normal levels of ATP production. The phrase "reverse energy failure" denotes that energy failure is reversed and/or that energy metabolism is returned or restored to a normal, non-pathological state, or is at least improved compared to the state or level that would be present if a treatment were not administered. For example, a "reversal of energy failure" may involve an increase in or restoration of mitochondrial function as a result of providing a patient with a gene that can reverse energy failure such as the exemplary FXN gene. In one embodiment, the invention relates to a method for preventing or treating cardiomyopathy due to energy failure in a subject in need thereof, comprising administering to the subject a therapeutically effective amount of a vector which comprises a nucleic acid sequence of a gene that can reverse the pathological effects of energy function, e.g. cardiomyopathy.

As used herein the term "cardiomyopathy due to energy failure" denotes one or more of a deterioration of the function of the myocardium leading to heart failure, cardiac remodelling, long-term high blood pressure, heart valve problems, impaired calcium cycling sensitivity, disturbed biochemical stress sensing, altered energy homeostasis due but not limited to mitochondrial dysfunction and fibrosis.

In a particular embodiment, the cardiomyopathy due to energy failure may be one or more of a dilated cardiomyopathy, a hypertrophic cardiomyopathy, a restrictive cardiomyopathy or an ischemic cardiomyopathy.

In another particular embodiment, the cardiomyopathy due to energy failure may be a cardiomyopathy due to a deficiency of fatty oxidation, including but not limited to primary carnitine deficiency, long-chain 3-hydroxyacyl-CoA dehydrogenase (LCHAD) deficiency, translocase deficiency, and very long-chain acyl-CoA dehydrogenase (VLCAD) deficiency.

In another particular embodiment, the cardiomyopathy due to energy failure may be a cardiomyopathy associated with Friedreich ataxia.

As used herein, the term "a gene that can reverse energy failure" denotes a nuclear or mitochondrial gene that can reverse energy failure and/or mitochondrial dysfunction.

In a particular embodiment, the gene that can reverse energy failure may be a nuclear gene encoding a subunit of pyruvate dehydrogenase complex, a nuclear or a mitochondrial gene coding for a subunit of Complex I, III, IV or V involved in oxidative phosphorylation; a mitochondrial gene encoding transfer RNA, a gene involved in the biogenesis of mitochondria such as SIRT1, a gene involved in the fusion of mitochondria such as OPA1, a gene involved in the fission of mitochondria such as FIS1 or a gene involved in the oxidation of fatty acid such as long-chain 3-hydroxyacyl-CoA dehydrogenase or very long-chain specific acyl-CoA dehydrogenase.

In a particular embodiment, the gene that can reverse energy failure is the frataxin (FXN) gene.

As used herein in its broadest meaning, the term "preventing" or "prevention" refers to preventing the disease or condition from occurring in a subject which has not yet been diagnosed as having it. The subject may, however, be known to be susceptible to developing the disease, e.g. may be known or suspected of harbouring a genetic mutation that may lead to the condition, even though overt clinical symptoms have not yet appeared.

As used herein, the term "treating" or "treatment" means reversing, alleviating, or inhibiting the progress of the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a patient is such an amount which induces, ameliorates, stabilises, slows down the progression or otherwise causes an improvement in the pathological symptoms, disease progression or physiological conditions associated with or resistance to succumbing to a disorder.

As used herein, the term "gene" refers to a polynucleotide containing at least one open reading frame that is capable of encoding a particular polypeptide or protein after being transcribed and translated.

As used herein, the terms "coding sequence", "a sequence which encodes a particular protein" or "encoding nucleic acid", denotes a nucleic acid sequence which is transcribed (in the case of DNA) and translated (in the case of mRNA) into a polypeptide in vitro or in vivo when placed under the control of (operably linked to) appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

In a particular embodiment, the invention relates to a method for preventing or treating a cardiomyopathy associated with Friedreich ataxia in a subject in need thereof, comprising administering to said subject of a therapeutically effective amount of a vector which comprises a frataxin (FXN) encoding nucleic acid.

The FXN gene encodes the protein frataxin. Frataxin is a protein localized to the mitochondrion and is involved in assembly of iron-sulfur clusters by regulating iron entry and the activity of cysteine desulfurase. A cDNA sequence for human FXN (transcript variant 1) is disclosed in Genbank Access Number NM_000144 or NG_008845 (SEQ ID NO:1). The amino acid sequence of human frataxin is shown in SEQ ID NO:2.

The sequence of the nucleic acid of the frataxin (cDNA) is:

(SEQ ID NO: 1)

```
agtctccctt gggtcagggg tcctggttgc actccgtgct ttgcacaaag caggctctcc attttgtta aatgcacgaa tagtgctaag ctgggaagtt cttcctgagg tctaacctct agctgctccc ccacagaaga gtgcctgcgg ccagtggcca ccaggggtcg ccgcagcacc cagcgctgga gggcggagcg ggcggcagac ccggagcagc atgtggactc tcgggcgccg cgcagtagcc ggcctcctgg cgtcacccag cccagcccag gcccagaccc tcacccgggt cccgcggccg gcagagttgg ccccactctg cggccgccgt ggcctgcgca ccgacatcga tgcgacctgc acgccccgcc gcgcaagttc gaaccaacgt ggcctcaacc agatttggaa tgtcaaaaag cagagtgtct atttgatgaa tttgaggaaa tctggaactt tgggccaccc aggctctcta gatgagacca cctatgaaag actagcagag gaaacgctgg actctttagc agagtttttt gaagaccttg cagacaagcc atacacgttt gaggactatg atgtctcctt tgggagtggt gtcttaactg tcaaactggg tggagatcta ggaacctatg tgatcaacaa gcagacgcca aacaagcaaa tctggctatc ttctccatcc agtggaccta agcgttatga ctggactggg aaaaactggg tgtactccca cgacggcgtg tccctccatg agctgctggc cgcagagctc actaaagcct
```

-continued

```
taaaaaccaa actggacttg tcttccttgg cctattccgg aaaagatgct tgatgcccag ccccgtttta aggacattaa aagctatcag gccaagaccc cagcttcatt atgcagctga ggtctgtttt ttgttgttgt tgttgtttat ttttttttatt cctgcttttg aggacagttg ggctatgtgt cacagctctg tagaaagaat gtgttgcctc ctaccttgcc cccaagttct gatttttaat ttctatggaa gattttttgg attgtcggat ttcctccctc acatgatacc cctatctttt tataatgtct tatgcctata cctgaatata caaccttta aaaagcaaa ataataagaa ggaaaaattc caggagggaa aatgaattgt cttcactctt cattctttga aggatttact gcaagaagta catgaagagc agctggtcaa cctgctcact gttctatctc caaatgagac acattaaagg gtagcctaca aatgttttca ggcttctttc aaagtgtaag cacttctgag ctctttagca ttgaagtgtc gaaagcaact cacacgggaa gatcatttct tatttgtgct ctgtgactgc caaggtgtgg cctgcactgg gttgtccagg gagacctagt gctgtttctc ccacatattc acatacgtgt ctgtgtgtat atatattttt tcaatttaaa ggttagtatg gaatcagctg ctacaagaat gcaaaaaat ttccaaagac aagaaaagag gaaaaaaagc cgttttcatg agctgagtga tgtagcgtaa caaacaaaat catggagctg aggaggtgcc ttgtaaacat gaaggggcag ataaaggaag gagatactca tgttgataaa gagagccctg gtcctagaca tagttcagcc acaaagtagt tgtcccttg tggacaagtt tcccaaattc cctggacctc tgcttcccca tctgttaaat gagagaatag agtatggttg attcccagca ttcagtggtc ctgtcaagca acctaacag ctagttctaa ttccctattg ggtagatgag gggatgacaa gaacagttt ttaagctata taggaaacat tgttattggt gttgccctat cgtgatttca gttgaattca tgtgaaaata atagccatcc ttggcctggc gcggtggctc acacctgtaa tcccagcact tttggaggcc aaggtgggtg gatcacctga ggtcaggagt tcaagaccag cctggccaac atgatgaaa cccgtctcta ctaaaaatac aaaaaattag ccgggcatga tggcaggtgc ctgtaatccc agctacttgg gaggctgaag cggaagaatc gcttgaaccc agaggtggag gttgcagtga gccgagatcg tgccattgca ctgtaacctg ggtgactgag caaaactctg tctcaaaata ataataacaa tataataata ataatagcca tcctttattg tacccttact gggttaatcg tattatacca cattcctca ttttaatttt tactgacctg cactttatac aaagcaacaa gcctccagga cattaaaatt catgcaaagt tatgctcatg ttatattatt ttcttactta agaaggatt tattagtggc tgggcatggt ggcgtgcacc tgtaatccca ggtactcagg aggctgagac gggagaattg cttgaccca ggcggaggag gttacagtga gtcgagatcg tacctgagcg acagagcgag actccgtctc aaaaaaaaaa aaaggaggg tttattaatg agaagtttgt attaatatgt agcaaaggct tttccaatgg gtgaataaaa acacattcca ttaagtcaag ctgggagcag tggcatatac ctatagtccc agctgcacag gaggctgaga caggaggatt gcttgaagcc aggaattgga gatcagcctg ggcaacacag caagatccta tctcttaaaa aaagaaaaa aaacctatta ataataaaac agtataaaca aaagctaaat aggtaaaata ttttttctga aataaaatta ttttttgagt ctgatggaaa tgtttaagtg cagtaggcca gtgccagtga gaaaataaat aacatcatac atgtttgtat gtgtttgcat cttgcttcta ctgaaagttt cagtgcaccc cacttactta gaactcggtg acatgatgta ctcctttatc tgggacacag cacaaaagag gtatgcagtg gggctgctct gacatgaaag tggaagttaa ggaatctggg ctcttatggg gtccttgtgg gccagccctt caggcctatt ttactttcat tttacatata gctctaattg gtttgattat ctcgttccca aggcagtggg agatccccat ttaaggaaag aaaaggggcc tggcacagtg gctcatgcct gtaatcccag cactttggga ggctgaggca gtgtatcac ctgaggtcag gagttcaaga ccagcctggc caacatggca aaatcccgtc tctactaaaa atattaaaaa attggctggg cgtggtggtt cgtgcctata atttcagcta ctcaggaggc tgaggcagga aatcgctgt aacctggggg gtggaggttg cagtgagacg agatcatgcc acttcactcc agcctggcca acagagcca actccgtctc aaataaataa ataaataaat aaagggactt caaacacatg aacagcagcc aggggaagaa tcaaaatcat attctgtcaa gcaaactgga aaagtaccac tgtgtgtacc aatagcctcc ccaccacaga ccctgggagc atcgcctcat ttatggtgtg gtccagtcat ccatgtgaag gatgagtttc caggaaaagg ttattaaata ttcactgtaa catactggag gaggtgagga attgcataat acaatcttag aaaacttttt ttcccctttt ctattttttg agacaggatc tcactttggc actcaggctg gaggacagtg gtacaatcaa agctcatggc agcctcgacc tccctgggct tgggcaatcc tcccacaggt gtgcacctcc atagctggct aatttgtgta ttttttgtag agatggggtt tcaccatgtt gcccaggctg gtctctaaca cttaggctca agtgatccac ctgcctcgtc ctcccaagat gctgggatta caggtgtgtg
```

-continued

```
ccacaggtgt tcatcagaaa gctttttcta ttatttttac cttcttgagt gggtagaacc tcagccacat agaaaataaa atgttctggc atgacttatt tagctctctg gaattacaaa gaaggaatga ggtgtgtaaa agagaacctg ggtttttgaa tcacaaattt agaatttaat cgaaactctg cctcttactt gtttgtagac actgacagtg gcctcatgtt tttttttttt ttaatctata aaatggagat atctaacatg ttgagcctgg gcccacaggc aaagcacaat cctgatgtga gaagtactca gttcatgaca actgttgttc tcacatgcat agcataattt catattcaca ttggaggact ctcccaaaa tatggatgac gttccctact caaccttgaa cttaatcaaa atactcagtt tacttaactt cgtattagat tctgattccc tggaaccatt tatcgtgtgc cttaccatgc ttatatttta cttgatcttt tgcataccct ctaaaactat tttagccaat ttaaaatttg acagtttgca ttaaattata ggtttacaat atgctttatc cagctatacc tgccccaaat tctgacagat gcttttgcca cctctaaagg aagacccatg ttcatagtga tggagtttgt gtggactaac catgcaaggt tgccaaggaa aaatcgcttt acgcttccaa ggtacacact aagatgaaag taatttttagt ccgtgtccag ttggattctt ggcacatagt tatcttctgc tagaacaaac taaaacagct acatgccagc aagggagaaa ggggaaggag gggcaaagtt ttgaaatttc atgtaaattt atgctgttca aaacgacgag ttcatgactt tgtgtataga gtaagaaatg ccttttcttt tttgagacag agtcttgctc tgtcacccag gctggagtgc agtggcacga tctgggctca ctacaacctc cgcctcctgg gttcaagcaa ttctctgcct cagcctcccg agtagctggg attacaggtg cctgccacca cacccggcta attttttgtat ttttagtaga cacggggttt caccatcatg gccaggctgg tcttgaactc ctgacctagt aatccacctg cctccgcctc ccaaagtgct gggattacag gcgtgagcca ctgcacccag ccagaaatgc cttctaatct ttggtttatc ttaattagcc aggacacttg gagtgcatcc cgaagtacct gatcagtggc cccctttggaa tgtgtaaaac tcagctcact tatatccctg catccgctac agagacagaa tccaagctca tatgttccat cttctctggc tgtatagttt aaggaatgga aggcaccaga acagatttat tgaaatgttt attagctgaa gatttattta gacagttgag gaaaacatca gcacccagca gtaaaattgg ctctcaaaga ttttcttctc ctgtggaaag tcagacctct gaggccccat ccaggtagaa gtactagtgc aagaagggcc tctgctgtcc acttgtgttt ctgtgatctg tgggaacatt gttaacgcca catcttgacc tcaaattgtt tagctcctgg ccagacacgg tggctcacac ctgtaatccc agcactttga gaggctgagg caggtggatc acctgaggtt aggagttcga ggccagcctg gtcaacatgg taaaaccccg cctctactaa aaatacaaaa attagctggc cgtagtggcg cacgcctgtt atcccagcta ctcgggaggc tgaggcagga gaattgcttg aacctgggtg gtggaggttg cagtgagccg agattacacc actgcactcc agcctgggtg acaagaggga aactccatta aaaaaatgta attcccgtgt ctgccatctt aagtgtaaag gtggctaaat tatatagaaa aataagacaa tatcatttcc caattacatt cctttcctac cgcactctat gatgctagct gagattttc caaaagaaaa tggcttaaat aaaacccta gagaaagaaa aactttaaat ccctccaaag ctcaaaagta atagaaacag atgagtttgg agtcaggatt tctctgtaag attgcctagg ctgtgtactg cacatctcca ggtgccactg ttgacagaga ttataactac aatgtgaagt gaatggtgcc actgacagtt atgcaaaccg tccagagcat agccacctga tcctgctggg attcctcttg ccagtccatc agcagttccc cttgaaagtt tcaccaaaca tcccttaaat ctgccctctc ctgcccgtcc ccagtggagg tcctcatcat ttttcacctg catttttgca ggagctttct tatatccacc ttcctccttt tctctcagcc catcatctag ctacacagtc tccagggtaa gctttcagaa aggcaatctc ttgtctgtaa aacctaagca ggaccaaggc caagtttctt agcctgaaaa atgtgctttt ctgactgaac tgttcaggca ctgactctac atataattat gcttttctac ccctcacac tcaacacttt gactccagca atcccaaatc cccagatccc taagtgtgct gtgctatttt cacgtggctc tcagacttgg ccagtgctgt ttccattttg gtctttattc cccacatctc tgcctggggg gtagattcta ccctgaaaaa tgttcttggc acagccttgc aaactcctcc tccactcagc ctctgcctgg atgcccttga ttgttccatg tcctcagcat accatgtttg tctttcccag cactgaccta ccatgtgtca ccctgcttg gctgtacctt ccatgaggct aggactatgt gtctcctttg ttgactgctg ttgccctagc atcttgcaca gttccttgca cacaattaga gctctataaa tgtcaaataa atgtgttata attatatgtt taagatagtt gttcaaataa actctaaata accccaac.
```

The sequence of the frataxin protein is (SEQ ID NO:2):

MWTLGRRAVAGLLASPSPAQAQTLTRVPRPAELAPLCGRRGLRTDIDATC

TPRRASSNQRGLNQIWNVKKQSVYLMNLRKSGTLGHPGSLDETTYERLAE

ETLDSLAEFFEDLADKPYTFEDYDVSFGSGVLTVKLGGDLGTYVINKQTP

NKQIWLSSPSSGPKRYDWTGKNWVYSHDGVSLHELLAAELTKALKTKLDL

SSLAYSGKDA.

In a particular embodiment, the invention provides a nucleic acid construct comprising a sequence that is or includes SEQ ID NO:1 or a variant thereof for treating cardiomyopathy associated with Friedreich ataxia.

The variants include, for instance, naturally-occurring variants due to allelic variations between individuals (e.g., polymorphisms), alternative splicing forms, in particular transcript variants 2 and 3 (GenBank accession numbers NM_001161706 and NM_181425), etc. The term variant also includes FXN gene sequences from other sources or organisms. Variants are preferably substantially homologous to SEQ ID NO:1, i.e., exhibit a nucleotide sequence identity of typically at least about 75%, preferably at least about 85%, more preferably at least about 90%, more preferably at least about 95%, 96%, 97%, 98%, or 99% with SEQ ID NO: 1. Variants of a FXN gene also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

In a particular embodiment, the variant may be a variant of the SEQ ID NO:1 which encodes for the amino acid sequence 81-210 of the SEQ ID NO:2 (named variant "81-210").

In a another particular embodiment, a sequence known as the "mitochondrion-targeting signal" or "mitochondrial targeting signal" may be added to a variant of the invention, for example to the variant "81-210". Sequences known as "mitochondrion-targeting signal" or "mitochondrial targeting signal" are referred to as MTS by the skilled person.

A MTS sequence can be identified within a protein or nucleic acid sequence by a person of ordinary skill in the art.

Most mitochondrion-targeting peptides consist of an N-terminal pre-sequence of about 15 to 100 residues, preferably of about 20 to 80 residues. They are enriched in arginine, leucine, serine and alanine. Mitochondrial pre-sequences show a statistical bias of positively charged amino acid residues, provided mostly through arginine residues; very few sequences contain negatively charged amino acids. Mitochondrion-targeting peptides also share an ability to form an amphilic alpha-helix.

A complete description of a method to identify a MTS is available in: M. G. Claros, P. Vincens, 1996 (Eur. J. Biochem. 241, 779-786 (1996), "Computational method to predict mitochondrially imported proteins and their targeting sequences"), the complete content of which is herein incorporated by reference.

In another embodiment, the invention relates to a method for treating or preventing diseases associated with frataxin deficiency in a subject in need therefore, comprising administering to said subject a therapeutically effective amount of a vector which comprises a nucleic acid encoding frataxin.

In another embodiment, the invention relates a method for preventing or treating cardiomyopathy due but not limited to a cause such as energy failure in a subject in need thereof, comprising administering to said subject a therapeutically effective amount of a vector which comprises a nucleic acid sequence of a gene that can reverse energy failure.

In another particular embodiment, the invention relates a method for preventing or treating cardiomyopathy due but not limited to a cause such as energy failure in a subject in need thereof, comprising administering to said subject a therapeutically effective amount of a vector which comprises a frataxin (FXN) encoding nucleic acid.

Non Viral Vectors

In a particular embodiment, the vector use according to the invention is a non viral vector. Typically, the non viral vector may be a plasmid which includes nucleic acid sequences encoding FXN gene, or variants thereof, as described above.

The Viral Vectors

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

Examples of viral vector include but are not limited to adenoviral, retroviral, lentiviral, herpesvirus and adeno-associated virus (AAV) vectors.

Such recombinant viruses may be produced by techniques known in the art, such as by transfecting packaging cells or by transient transfection with helper plasmids or viruses. Typical examples of virus packaging cells include but are not limited to PA317 cells, PsiCRIP cells, GPenv+ cells, 293 cells, etc. Detailed protocols for producing such replication-defective recombinant viruses may be found for instance in WO95/14785, WO96/22378, U.S. Pat. No. 5,882,877, U.S. Pat. No. 6,013,516, U.S. Pat. No. 4,861,719, U.S. Pat. No. 5,278,056 and WO94/19478, the complete contents of each of which is hereby incorporated by reference.

In one embodiment, adeno-associated viral (AAV) vectors are employed.

In other embodiments, the AAV vector is AAV1, AAV2, AAV3, AAV4, AA5, AAV6, AAV7, AAV8, AAV9, AAVrh10 or any other serotypes of AAV that can infect humans, monkeys or other species.

In an exemplary embodiment, the AAV vector is an AAVrh10.

By an "AAV vector" is meant a vector derived from an adeno-associated virus serotype, including without limitation, AAV-1, AAV-2, AAV-3, AAV-4, AAV-5, AAV6, etc. AAV vectors can have one or more of the AAV wild-type genes deleted in whole or part, preferably the rep and/or cap genes, but retain functional flanking inverted terminal repeat (ITR) sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g by the insertion, deletion or substitution of nucleotides, as long as the sequences provide for functional rescue, replication and packaging. AAV expression vectors are constructed using known techniques to at least provide as operatively linked components in the direction of transcription, control elements including a transcriptional initiation region, the DNA of interest (i.e. the FXN gene) and a transcriptional termination region.

The control elements are selected to be functional in a mammalian cell. The resulting construct which contains the operatively linked components is bounded (5' and 3') with functional AAV ITR sequences. By "adeno-associated virus inverted terminal repeats" or "AAVITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds., the complete contents of which is hereby incorporated by reference) for the AAV-2 sequence. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV-6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV-6, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Particularly preferred are vectors derived from AAV serotypes having tropism for and high transduction efficiencies in cells of the mammalian myocardium, particularly cardiomyocytes and cardiomyocyte progenitors. A review and comparison of transduction efficiencies of different serotypes is provided in Cearley C N et al., Moleuclar Therapy 16(10); 1710-1718, 2008, the complete contents of which is hereby incorporated by reference. In other non-limiting examples, preferred vectors include vectors derived from any serotypes like AAV1, AAV2, AAV3, AAV4, AA5, AAV6, AAV7, AAV8, AAV9, or AAVrh10, which have also been shown to transduce cells of cardiomyocytes.

The selected nucleotide sequence is operably linked to control elements that direct the transcription or expression thereof in the subject in vivo. Such control elements can comprise control sequences normally associated with the selected gene.

Alternatively, heterologous control sequences can be employed. Useful heterologous control sequences generally include those derived from sequences encoding mammalian or viral genes. Examples include, but are not limited to, the phophoglycerate kinase (PKG) promoter, CAG (chicken beta-actin promoter with CMV enhancer) promoter, MCK (muscle creatine kinase) promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. The promoters can be of human origin or from other species, including from mice. In addition, sequences derived from nonviral genes, such as the murine metallothionein gene, will also find use herein. Such promoter sequences are commercially available from, e.g. Stratagene (San Diego, Calif.).

Examples of heterologous promoters include but are not limited to the CMV promoter.

Examples of inducible promoters include but are not limited to DNA responsive elements for ecdysone, tetracycline, and hypoxia andaufin.

The AAV expression vector which harbors the DNA molecule of interest bounded by AAV ITRs, can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g. U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994, the complete contents of each of which is hereby incorporated by reference. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g. U.S. Pat. No. 5,139, 941, the complete contents of which is hereby incorporated by reference. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge Nature, vol. 292, 1981, page 756; Nambair et al. Science, vol. 223, 1984, page 1299; Jay et al. J. Biol. Chem. vol. 259, 1984, page 6311, the complete contents of each of which is hereby incorporated by reference. In order to produce AAV virions, an AAV expression vector is introduced into a suitable host cell using known techniques, such as by transfection. A number of transfection techniques are generally known in the art. See, e.g. Graham et al, Virology, 52, 456-467, (1973); Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Feigner et al., 1987, PNAS USA, 84, 21, 7413-17), and nucleic acid delivery using high-velocity microprojectiles (Klein et al., 1987, m Endocrinology 120:2339-45). The complete contents of each of the foregoing references are hereby incorporated by reference in entirety.

For instance, a preferred viral vector, such as the AAVrh10, comprises, in addition to a FXN encoding nucleic acid sequence, the backbone of AAV vector with ITR derived from AAV-2, the promoter, such as the mouse PGK (phosphoglycerate kinase) gene or the cytomegalovirus/β-actin hybrid promoter (CAG) consisting of the enhancer from the cytomegalovirus immediate gene, the promoter, splice donor and intron from the chicken β-actin gene, the splice acceptor from rabbit β-globin, or any promoter such as PGK, CAG, MCK.

Delivery of the Vectors

It is herein provided a method for treating cardiomyopathy due to energy failure in a subject, said method comprising:
(a) providing a vector as defined above, which comprises a nucleic acid sequence of a gene that can reverse energy failure; and
(b) delivering the vector to the subject in need thereof and whereby the gene is expressed by the transduced cells at a therapeutically effective level.

In a particular embodiment, a method for treating cardiomyopathy associated with Friedreich ataxia in a subject is herein provided, said method comprising:
(a) providing a vector as defined above, which comprises a FXN encoding nucleic acid; and
(b) delivering the vector to the subject in need thereof and whereby FXN is expressed by the transduced cells at a therapeutically effective level.

In a particular method, the vector is delivered directly into the myocardium by epicardiac injection followed by minithoracotomy, by intracoronary injection, by endomyocardic injection or by another type of injection useful in the heart.

Additional routes of administration may also comprise local application of the vector under direct visualization, e.g., superficial cortical application, or other nonstereotactic application. The vector may also be delivered, for example, intrathecally, into the ventricules or by intravenous injection.

The target cells of the vectors of the present invention are cells of the myocardium of a subject afflicted with a cardiomyopathy associated with Friedreich ataxia. Preferably the subject is a human being, adult or child. However, veterinary applications are also contemplated.

However the invention encompasses delivering the vector to biological models of the disease. In that case, the biological model may be any mammal at any stage of development at the time of delivery, e.g., embryonic, fetal, infantile, juvenile or adult. Furthermore, the target myocardium cells may be essentially from any source, especially any cells derived from hiPS from FRDA patients, nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

The vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but are not limited to water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

The preferred doses and regimen may be determined by a physician, and depend on the age, sex, weight, of the subject, and the stage of the disease. As an example, for delivery of a nucleic acid sequence encoding an FXN polypeptide using a viral expression vector, each unit dosage of FXN polypeptide expressing vector may comprise 2.5 to 100 µl of a composition including a viral expression vector in a pharmaceutically acceptable fluid at a concentration ranging from $10^{11}$ to $10^{16}$ viral genome per ml, for example.

Pharmaceutical Composition

A second object of the invention concerns a pharmaceutical composition for preventing or treating cardiomyopathy due to energy failure in a subject in need thereof, which comprises a therapeutically effective amount of a vector which comprises a nucleic acid sequence of a gene that can reverse energy failure.

In a particular embodiment, the invention concerns a pharmaceutical composition for preventing or treating cardiomyopathy associated with Friedreich ataxia in a subject in need thereof, which comprises a therapeutically effective amount of a vector which comprises a FXN encoding nucleic acid.

By a "therapeutically effective amount" is meant a sufficient amount of the vector of the invention to treat a cardiomyopathy associated with Friedreich ataxia at a reasonable benefit/risk ratio applicable to any medical treatment.

It will be understood that the single dosage or the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific nucleic acid or polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range per adult per day.

The therapeutically effective amount of the vector according to the invention that should be administered, as well as the dosage for the treatment of a pathological condition with the number of viral or non-viral particles and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the vector according to the invention may be in any form that is suitable for the selected mode of administration, for example, for intraventricular, intramyocardium, intracoronary or intravenous administration.

In the pharmaceutical compositions of the present invention for intramuscular, intravenous, intramyocardium, intracoronary or intraventricular administration, the active principle, alone or in combination with one or more other active principles, can be administered in a unit administration form, as a mixture with conventional pharmaceutical supports, to animals and human beings.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The vector according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Multiple doses can also be administered.

In another embodiment, the invention relates to a pharmaceutical composition for treating or preventing diseases associated with frataxin deficiency in a subject in need therefore, comprising administering to said subject a therapeutically effective amount of a vector which comprises a nucleic acid encoding frataxin.

The invention will be further illustrated by the following figures and examples. However, these examples and figures should not be interpreted in any way as limiting the scope of the present invention.

FIGURES

FIG. 1 A, FIG. 1 B1, FIG. 1 B2. Administration of AAVrh10.CAG-hXN vector at 3 weeks of age prevents the onset of cardiac failure and rescues survival in pre-symptomatic MCK mice. (FIG. 1 A) Survival rates of wild-type (black solid line), treated (grey dotted line) and untreated (black dotted line) MCK mice. n=9-10 for each group. 100% survival was observed for wild type and treated mice up to 35 weeks and thus the two lines (i.e. the grey dotted line and the black dotted line) are superimposed near the top of the graph. (FIG. 1 B1 and FIG. 1 B2) Relative quantification of atrial natriuretic peptide (ANP), brain natriuretic peptide (BNP) and sarcoplasmic reticulum $Ca^{2+}$ ATPase (Serca2a) mRNA expressions in heart at 8 and 35 weeks for wild-type (white), treated (grey) and untreated (black) MCK mice; n=3-5 per group (*$P<0.05$; ***$P<0.001$). mRNA expression was normalized to 18S ribosomal RNA and is presented as a fold change relative to wild-type values. Data are represented as means±SD.

FIG. 2 A1, FIG. 2 A2, FIG. 2 B1, FIG. 2 B2, FIG. 2 C, FIG. 2 D. Administration of AAVrh10.CAG-hXN vector at 7 weeks of age in symptomatic MCK mice with severe cardiac failure reverses the cardiac contractile dysfunction, Fe—S cluster proteins, and cardiomyocyte and mitochondrial ultrastructure disorganization. (FIG. 2 A1 and FIG. 2 A2) Longitudinal echocardiographic assessment of the left ventricle mass (LVM, left) and the shortening fraction (SF, right) for wild-type (black circles) mice, treated (light grey squares) and untreated (grey triangle) MCK mice. Data are represented as means±SD. n=9-11 for each group. (FIG. 2 B1 and FIG. 2 B2) Survival rates of wild-type mice (black solid line), treated (grey dotted line) and untreated (black dotted line) MCK mice. n=9-11 for each group. (FIG. 2 C) Relative quantification of atrial natriuretic peptide (ANP), brain natriuretic peptide (BNP) and sarcoplasmic reticulum $Ca^{2+}$ ATPase (Serca2a) mRNA expressions in heart at 8, 15 and 22 weeks for wild-type (white), treated (grey) and untreated (black) MCK mice; n=3-5 per group and per age (*P<0.05; P<0.01; ns: statistically non-significant). mRNA expression was normalized to 18S ribosomal RNA and is presented as a fold change relative to wild-type values. Data are represented as means±SD. (FIG. 2 D) Biochemical measurements of combined cytosolic and mitochondrial aconitases (Aco) and succinate dehydrogenase (SDH, complex II) activities in heart from wild-type (white) mice, treated (grey) and untreated (black) MCK mice at 8, 15 and 22 weeks of age; n=3-6 per group and per age (P<0.01). Isocitrate dehydrogenase (IDH) activity was used to normalize SDH and aconitase activities for total mitochondrial content.

EXAMPLES

Material & Methods

Adeno-Associated Viral Vector Construction and Production

Human frataxin (hFXN) cDNA, including the mitochondrial targeting sequence, fused to a HA tag was subcloned in a pAAV2-CAG plasmid (Sondhi, Hackett et al. 2007) to produce pAAV2-CAG-hFXN that included the viral inverted terminal repeat (ITR) from AAV2; the cytomegalovirus/β-actin hybrid promoter, consisting of the enhancer from the cytomegalo-virus immediate-early gene, the promoter, splice donor, and intron from the chicken β-actin gene, and the splice acceptor from rabbit β-globin. The AAVrh10.CAG-hFXN-HA vector was produced as described earlier (Rabinowitz, Rolling et al. 2002) in the Vector Core at the University Hospital of Nantes (http://www.vectors.nantes.inserm.fr). The final titers of the two batches used were $5.4 \times 10^{12}$ vg/ml and $2.15 \times 10^{13}$ vg/ml, respectively.

Animal Procedures

Mice with a specific deletion of Fxn gene in cardiac and skeletal muscle (MCK-Cre-FxnL3/L-) (MCK mice) in 100% C57BL/6J background were generated and genotyped as previously described (Puccio, Simon et al. 2001). Mice were maintained in a temperature and humidity controlled animal facility, with a 12 hours light/dark cycle and free access to water and a standard rodent chow (D03, SAFE, Villemoisson-sur-Orge, France). All animal procedures and experiments were approved by the local ethical committee for Animal Care and Use (Com'Eth 2011-07), and were performed in accordance with the Guide for the Care and Use of Laboratory Animals (National Institutes of Health). For biodistribution studies, three weeks old wild-type mice were anesthetized by intraperitoneal injection of ketamine/xylazine (75/10 mg/kg) to allow intravenous administration by retro-orbital injection of AAVrh10.CAG-FXN at a dose of $5.10^{13}$ vg/kg, and sacrificed at 7 weeks of age (4 weeks post-injection). For gene therapy studies, three or seven weeks old MCK mice were anesthetized by intraperitoneal injection of ketamine/xylazine (75/10 mg/kg or 60/8 mg/kg, respectively) to allow intravenous administration by retro-orbital injection of AAVrh10.CAG-FXN at a dose of $5.10^{13}$ vg/kg. Untreated MCK and WT mice littermates were injected with equivalent volume of saline solution. Survival was evaluated daily and mice weight weekly. The mice cardiac function was evaluated under isofluorane anesthesia (1-2%) by echocardiography by an experimenter blinded to mice genotype and treatment regimen, as previously described (Seznec, Simon et al. 2004). Animals were killed by $CO_2$ inhalation at 8, 15, 22 or 35 weeks, and tissues samples for biochemical and molecular analysis were immediately frozen in liquid nitrogen. For histological analysis, mice were anesthetized by intraperitoneal injection of ketamine/xylazine and perfused with cooled saline solution. For histological analysis of dorsal root ganglia, spinal cord and cardiac tissue was embedded in OCT Tissue Tek (Sakura Finetechnical, Torrance, Calif.) and snap-frozen in isopentane chilled in liquid nitrogen. Samples of skeletal muscles were directly snap-frozen in isopentane chilled in liquid nitrogen. For electron microscopy analysis, small samples from the middle of left ventricle and its apex were collected, then fixed and embedded in Epon as previously described (Puccio, Simon et al. 2001).

Histopathology, Enzyme Histochemistry and Electron Microscopy

For histochemical analysis, 10 μm cryosections were stained either with hematoxylin and eosin (H&E), Sirius red and Fast green to label extracellular collagen, or DAB enhanced Perls to label iron ($Fe^{3+}$) deposits (Puccio, Simon et al. 2001).

Sirius red and fast green staining: Tissue sections were fixed with 10% paraformaldehyde in 0.1 M phosphate buffer (PBS), pH 7.4 for 10 min and then incubated with a saturated solution of picric acid containing 0.1% Direct red 80 (Sigma) for 2 min, washed with 0.5% glacial acetic acid solution followed by deionized water, and subsequently incubated in 0.05% Fast Green solution for 5 min, and then washed with 0.5% glacial acetic acid solution. Finally, sections were dehydrated in graded alcohols, cleared in Histosol Plus (Shandom) for 5 min and mounted using Pertex mounting medium (Histolab Products AB).

DAB-enhanced Perls iron staining: Tissue sections were fixed with 10% paraformaldehyde in 0.1 M phosphate buffer (PBS), pH 7.4 for 20 min and incubated in Perls solution (1% HCl, 1% Potassium Ferrocyanide) for 30 min. Staining was enhanced by incubation in 0.025% 3'-3'-diaminobenzidine tetrahydrochloride (Sigma-Aldrich), 0.005% H2O2 in PBS buffer for 30 min, and then developed in the same buffer. Finally, sections were dehydrated in graded alcohols, cleared in Histosol Plus (Shandom) for 5 min and mounted using Pertex mounting medium (Histolab Products AB).

Enzyme histochemical analyses: Succinate dehydrogenase (SDH) and Cytochrome C Oxydase (COX) activities were performed on 10 μm cryostat sections of tissues, as previously described (Puccio, Simon et al. 2001).

Electron microscopy analysis: Ultrathin sections (70 nm) of cardiac tissue were contrasted with uranyl acetate and lead citrate and examined with a Morgagni 268D electron microscope, as described previously (Puccio, Simon et al. 2001).

Immunofluorescence and Image Acquisition

Cardiac and spinal cord tissue cryosections were fixed in 4% PFA for 10 min, washed and then permeabilized in methanol at −20° C. for 20 min. Sections were blocked and permeabilized at the same time with PBS, 1% NGS, 5% BSA, 0.3% Triton X-100 for 1 h at room temperature (RT) and then washed in PBS, 0.2% Tween 1% BSA 1% NGS (PBS-TBN). Subsequently, tissues were incubated overnight (O/N) at 4° C. with the rabbit polyclonal antibody against frataxin (FXN935)(1/250) diluted in PBS-TBN (Puccio, Simon et al. 2001). The Alexa fluor-594 goat anti-rabbit antibody (1/500) (Molecular Probes) was incubated for 2 h at RT. Sections were stained with Hoechst and mounted using Aqua-Polymount mounting medium (Polysciences, Inc.). For co-immunolabelling of HA-tag and prohibitin, the tissue section were washed in PBS, 0.05% Tween and then blocked O/N at 4° C. in M.O.M.™ Mouse Ig Blocking Reagent (Vector Laboratories). Section were then incubated O/N at 4° C. with the mouse monoclonal antibody to HA tag (1/150) (Covence) diluted in M.O.M.™ diluent (Vector Laboratories). After washing, sections were incubated for 1 h at RT with the goat anti-mouse antibody conjugated to Alexa Fluor-594 nm (1/500) (Molecular Probes) diluted in M.O.M.™ diluent. Subsequently, sections were washed and blocked in PBS, 0.3% Triton, 2% NGS for 1 h 30 at RT, washed and incubated for 2 h at RT with the rabbit polyclonal antibody to prohibitin (1/150) (Abcam) diluted in PBS-BTN. The Alexa Fluor-488 nm goat anti-rabbit antibody (1/500) (Molecular Probes) was incubated 1 h 30 at RT with the goat anti-rabbit antibody conjugated to Alexa Fluor-488 nm (Molecular Probes) diluted at 1/500 in PBS-BTN. Sections were stained with Hoechst and mounted using Aqua-Polymount mounting medium (Polysciences, Inc).

Confocal analysis was performed on a Leica TCS SP2 upright confocal microsystem with a Plan Apo CS (numerical aperture 1.4) 63× objective. Observation of whole cardiac cryosections was performed on a Leica Z16 APO A microsystem fitted with a QuanteM-S12SC camera and combined with a 2× objective (39 mm working distance).

Quantitative Real-Time PCR Total

Total RNA was extracted from frozen heart pulverized with the Precellys24 homogeniser (Bertin Technologies) and using TRI Reagent (MRC) according to the manufacturer's protocol and was treated with DNAse I treatment (Roche Biosciences). cDNA was generated by reverse transcription using the Transcriptor Fist strand cDNA synthesis kit (Roche biosciences). Quantitative RT-PCR was performed using the SYBR Green I Master (Roche biosciences) and light Cycler 480 (Roche biosciences) with primers described in Supplementary Table S3. 18S ribosomal RNA was used as internal standard.

Enzyme Activities

Tissues were immediately frozen in liquid nitrogen. The activities of the respiratory chain enzyme SDH (complex II), the citric acid cycle enzymes isocitrate dehydrogenase, and mitochondrial and cytosolic aconitases were determined as described (Puccio, Simon et al. 2001).

Immunoblot Analysis

Extracts of tissues were frozen in liquid nitrogen, and then homogenized in lysis buffer containing Tris-HCl (280 mM, pH 6.8), 10% SDS, 50% glycerol. Total protein extract (10 µg or 50 µg) was analyzed on SDS-glycine polyacrylamide gels. Proteins were transferred to nitrocellulose membranes blocked with 5% non-fat milk and then incubated with the different primary antibodies, polyclonal anti-frataxin (R1250 purified sera IGBMC, 1/1,000), anti-HA (Covance, 1/500), anti-mitochondrial aconitase (R2377 purified sera IGBMC, 1/20,000), anti-Ndufs3 (Invitrogen, 1/4,000), anti-SDH (Invitrogen, 1/4,000), anti-Rieske (Abcam, 1/5,000), anti-lipoic acid (Calbiochem, 1/5,000), anti-GAPDH (Millipore, 1/10,000) and monoclonal anti-beta-tubulin (2A2, IGBMC 1/1,000). Secondary antibody (goat anti-rabbit or anti-mouse IgG, respectively) coupled to peroxidase was diluted at 1/5,000 and used for detection of the reaction with Supersignal Substrate Western blotting (Pierce), according to the manufacturer's instructions.

Statistical Analysis

All data are presented as mean±standard deviation of the mean (SD). Statistical analysis was carried out using Statview software (SAS Institute Inc). For statistical comparison of three experimental groups, one-way ANOVA followed by Scheffe's post-hoc test was used. A value of $P<0.05$ was considered significant. For statistical comparison of two experimental groups, the bilateral Student's t-test was used. $P<0.05$ was considered significant.

Quantitative PCR on Genomic DNA

Genomic DNA was extracted from heart by using a phenol-chloroform method. AAVrh10.CAG-FXN vector genome copy numbers were measured by quantitative PCR using the SYBR Green I Master (Roche Biosciences) and light Cycler 480 (Roche Biosciences). The vector genome copy number per cell (VGC) was evaluated as described (Piguet, Sondhi et al. 2012). The mouse genomic Adck3 sequence was used as internal control.

Results

Three week-old MCK mice that do not exhibit yet any clinical, echocardiographic nor biochemical signs of cardiac disease, received a single intravenous injection of AAVrh10-CAG-hFXN at the dose of 5.4.1013 vg/kg (n=9). Serial echocardiographic measurements identified that the treatment efficiently prevented the development of the cardiac disease associated with frataxin deficiency. While untreated MCK mice developed a rapidly progressing left ventricle hypertrophy associated with a massive geometric remodeling characterized by increased left-ventricular diastolic diameter, the treated MCK mice were indistinguishable from wild-type (WT) littermate animals (data not shown). In parallel, systolic function evaluated by the left-ventricular shortening fraction (SF) and the cardiac output gradually decreased in untreated mice, while the treated MCK mice showed no sign of altered ventricular contractility (data not shown). The absence of echocardiographic phenotype in the treated MCK mice led to normal growth (data not shown) and survival (35 weeks with no sign of disease), in contrast to untreated mice which die at 65±10 days (FIG. 1A). To assess the cellular and molecular state of the cardiomyocytes, treated MCK mice were sacrificed at 35 weeks of age i.e. more than triple lifespan of untreated mice. Consistent with the evolution towards heart failure, the expression of atrial natriuretic peptide (ANP) and the brain natriuretic peptide (BNP), two markers of pathology-induced stress program induced by hemodynamic overload was markedly increased in the heart from untreated mice at 8 weeks compared to WT (19 and 7 times, respectively, $p<0.001$) (FIG. 1B). In contrast, no difference could be detected in the expression level of these two markers between the treated MCK mice and the WT littermates, supporting the absence of pathology-induced stress programme due to hemodynamic overload (FIG. 1B). Furthermore, while the expression of sarcoplasmic reticulum $Ca^{2+}$ ATPase (Serca2a), a critical determinant of cardiac relaxation responsible for diastolic $Ca^{2+}$ reuptake from cytosol was reduced in untreated mice (3.3 fold, $p<0.01$), treated MCK mice had normal Serca2a levels (FIG. 1C). Histological analysis confirmed a preserved overall heart organization in 35 week-old treated MCK mice, compared to the myocardial degeneration with cytoplasmic vacuolization in the necrotic cardiomyocytes observed in untreated mice at 8 weeks of age (data not shown). Furthermore, Sirius-red staining (data not shown) and collagen type I and III mRNA expression (data not shown) indicated the absence of myocardial post-necrotic fibrosis in treated animals, in comparison to the massive interstitial fibrosis present in untreated MCK mice at 8 weeks (data not shown).

Intravenous injection of AAVrh10-FXN led to robust viral transduction of the heart (20.85±6.3 vg/cell) and liver, but also of skeletal muscle and dorsal root ganglia (data not shown). Western blot analysis using an anti-FXN antibody, which equally detects human and mouse frataxins, demonstrated a significant overexpression (>10 fold) of AAVrh10-encoded frataxin compared to endogenous frataxin of WT mice (data not shown). Sustained expression of the AAVrh10-encoded frataxin was seen over 35 weeks (data not shown). Mitochondrial import and maturation of frataxin was complete and non-saturated, as only the cleaved mature form of human frataxin was detected (data not shown). Immunohistochemistry analysis using both anti-FXN and anti-HA antibodies showed a broad expression of human frataxin throughout the heart of the AAV treated MCK mice, with close to 100% of transduced cardiomyocytes in the LV, RV and septum, with some cardiomyocytes expressing higher levels (data not shown). Co-localization with prohibitin demonstrated the expected mitochondrial localization of human frataxin (data not shown).

In line with the essential function of frataxin in regulating cellular Fe—S cluster biogenesis, it is now commonly accepted that frataxin deficiency leads to a primary Fe—S cluster deficit followed by secondary mitochondrial iron accumulation. Indeed, while untreated MCK mice showed a strong deficit in the Fe—S mitochondrial aconitase (mAco) and succinate dehydrogenase (SDH) (41.3% and 79.8%, respectively) (data not shown), treated mice presented levels of activities similar to WT littermates. Consistent with the widespread expression of hFXN in the heart after AAVrh10-CAG-hFXN injection, colorimetric staining of SDH activity confirmed the correction of Fe—S biogenesis in over 95% of cardiomyocytes (data not shown). While a substantial decrease in the levels of all analysed mitochondrial Fe—S proteins, was detected in untreated mice, as a result of the instability of the respective Fe—S apo-proteins, treated mutants had levels equivalent to WT (data not shown). Similarly, expression of human frataxin prevented the decrease in activity of the Fe—S enzyme lipoic acid synthase, indirectly demonstrated by normal levels of lipoic acid bound α-ketoglutarate dehydrogenase (KGDH) and pyruvate dehydrogenase (PDH) in treated animals in comparison to untreated animals (data not shown). Consistent with the absence of Fe—S cluster deficit, no cellular iron accumulation was observed in the cardiac tissue of treated mice (data not shown). Furthermore, we did not detect any sign of cellular iron homeostasis perturbation in treated animals (data not shown). Finally, electron microscopy analysis demonstrated a normal sarcomere organization of the cardiomyocytes and mitochondria ultrastructure in treated mice. Untreated animals showed sparse atrophied myofibrils and massive mitochondrial proliferation with abnormal collapsed or swollen cristae and iron accumulation (data not shown). All together, these data indicate that human frataxin gene transfer using AAVrh10 in pre-symptomatic MCK mice prevented the development of the mitochondrial FRDA cardiomyopathy at the molecular, cellular and physiological level.

While preventing the onset of the cardiomyopathy is an important step, at a clinical point of view it appears crucial to determine the therapeutic potential of this gene therapy approach when cardiac dysfunction is already present. Mutant MCK mice were intravenously injected with AAVrh10-CAG-hFXN at the dose of $5.4.10^{13}$ vg/kg (n=9) at 7 weeks, when the ventricular remodeling and left ventricular systolic dysfunction are established, with a major decrease in cardiac output ($60\pm9\%$ versus control values), attesting of cardiac failure. One week after injection at 8 weeks of age, the LV function was already significantly improved, with a $49\pm5\%$ ejection fraction and a decrease in LV hypertrophy and dilation in the treated mutant mice, whereas untreated animals presented typical signs of heart failure (FIG. 2A). Echocardiographic parameters regarding cardiac function progressively improved to reach WT values at 11-12 weeks of age, demonstrating a complete recovery of the ventricular systolic function and anatomy. The survival of the mice was significantly prolonged until at least 18 weeks of age (FIG. 2B). In accordance with the rapid reversion observed by echocardiography, human FXN was already strongly expressed one week after injection in heart of treated mutant mice and sustained over 22 weeks, with a mitochondrial localization (data not shown). Similarly, the pathology-induced stress program induced by hemodynamic overload, reflected by the expression of ANP and BNP, was significantly decreased one week after injection (8 weeks) in treated mice (FIG. 2C). By 22 weeks, the expression level of ANP and BNP of treated MCK mice was close to the expression level of WT animals, suggesting a normalization of the hemodynamic load. Furthermore, the expression of Serca2a progressively increased in treated mice between 8 and 22 weeks, indicating that diastolic $Ca^{2+}$ transport was likely restored (FIG. 2C). The reversal and correction of the cardiac phenotype correlated with a progressive increased in Fe—S proteins activities, mAco and SDH, in levels of the Fe—S proteins Ndufs3, SDH, Rieske, as well as in the lipoic acid bound PDH and KGDH (FIG. 2D). At 22 weeks, some rare patches with low SDH activity were detected in the cardiac tissue of treated mice (data not shown), corresponding to fibrotic scar probably already present at the time of treated. Interestingly, collagen staining and expression (type I and III) showed that interstitial cardiac fibrosis stopped one week post injection (data not shown). Strikingly, a rapid correction of the ultrastructure of the cardiac muscle was also observed one week after injection, with normal sarcomere organization and with a massive decrease in mitochondria (data not shown). In correlation with a still incomplete recovery of the biochemical phenotype one week after treatment, the mitochondria in the treated animals showed some signs of pathology, with the presence of some swollen mitochondria presenting parallel stacks of cristae membranes (data not shown). However, by 22 weeks, sarcomeres and mitochondria organizations completely recovered with no sign of pathological change. All together, these data indicate that AAVrh10.CAG-hFXN treatment in symptomatic MCK mice resulted in a rapid clinical, echocardiographic and biochemical improvement with a complete correction of the FRDA cardiomyopathy.

Conclusion

Our data demonstrates that AAVrh10-mediated transfer of hFXN gene in the myocardium of a mouse model of severe FRDA cardiomyopathy not only prevents the onset of the disease for a sustained period, but also can reverse heart failure and cardiac remodelling. The correction is extremely rapid and efficient, with a striking reversal of the mitochondrial abnormalities and biochemical Fe—S proteins deficit one week after treatment. Despite the severity of cardiac insufficiency at the time of treatment, the cardiac recovery is rapidly progressive, reaching normality within 4-5 weeks of treatment.

Indeed, the correction of mitochondrial dysfunction in the mouse was associated with a progressive increase of sarcoplasmic reticulum $Ca^{2+}$-ATPase (Serca2a) gene expression involved in sarcoplasmic reticulum calcium uptake from cytosol. Interestingly, a decrease in the expression and activity of Serca2a has been identified in cardiomyocytes from failing human hearts. A rapid correction of the ultrastructure of the cardiac muscle was also observed and interstitial cardiac fibrosis was stopped one week after treatment, preventing the dilation and massive remodelling of the cardiac tissue.

Fibrosis is an early manifestation of FRDA cardiomyopathy and its importance in organ pathology and dysfunction is relevant to a wide variety of diseases, including heart diseases.

In conclusion, delivery of a vector encoding hFXN in a mammalian model of FRDA cardiomyopathy resulted in i) prevention of the development of disease symptoms in asymptomatic individuals and ii) reversal of disease symptoms in individuals who already exhibited cardiomyopathy, biochemical Fe—S cluster impairment, mitochondrial dysfunction and interstitial cardiac fibrosis.

Thus, a gene that can reverse energy failure may be used for the treatment and the prevention of a cardiomyopathy due to energy failure (like the use of FXN gene in the case of cardiomyopathy associated with Friedreich ataxia as explained in the examples).

REFERENCES

Throughout this application, various references, including United States patents and patent applications, describe the state of the art to which this invention pertains. The disclosures of these references are hereby incorporated by reference in entirety into the present disclosure.

C. L. Tsai, D. P. Barondeau, Human frataxin is an allosteric switch that activates the Fe—S cluster biosynthetic complex. Biochemistry 49, 9132 (Nov. 2, 2010).

D. Simon, Seznec H, Gansmuller A, Carelle N, Weber P, Metzger D, Rustin P, Koenig M, Puccio H. Friedreich ataxia mouse models with progressive cerebellar and sensory ataxia reveal autophagic neurodegeneration in dorsal root ganglia. J. Neurosci. 2004 Feb. 25; 24(8): 1987-95.

D. Sondhi, N. R. Hackett, et al. (2007). "Enhanced survival of the LINCL mouse following CLN2 gene transfer using the rh.10 rhesus macaque-derived adeno-associated virus vector." Molecular therapy: the journal of the American Society of Gene Therapy 15(3): 481-491.

F. Colin, Martelli A, Clémancey M, Latour J M, Gambarelli S, Zeppieri L, Birck C, Page A, Puccio H, Ollagnier de Choudens S. Mammalian Frataxin Controls Sulfur Production and Iron Entry during de Novo Fe(4)S(4) Cluster Assembly. J Am Chem. Soc. 2013 Jan. 16; 135(2):733-40.

F. Piguet, D. Sondhi, et al. (2012). "Correction of brain oligodendrocytes by AAVrh.10 intracerebral gene therapy in metachromatic leukodystrophy mice." Human gene therapy 23(8): 903-914.

H. Puccio, Simon D, Cossée M, Criqui-Filipe P, Tiziano F, Melki J, Hindelang C, Matyas R, Rustin P, Koenig M. Mouse models for Friedreich ataxia exhibit cardiomyopathy, sensory nerve defect and Fe—S enzyme deficiency followed by intramitochondrial iron deposits. Nat. Genet. 2001 February; 27(2):181-6.

H. Puccio, D. Simon, et al. (2001). "Mouse models for Friedreich ataxia exhibit cardiomyopathy, sensory nerve defect and Fe—S enzyme deficiency followed by intramitochondrial iron deposits." Nat Genet. 27(2): 181-186.

H. Puccio et al., Mouse models for Friedreich ataxia exhibit cardiomyopathy, sensory nerve defect and Fe—S enzyme deficiency followed by intramitochondrial iron deposits. Nat Genet. 27, 181 (February, 2001).

H. Seznec et al., Idebenone delays the onset of cardiac functional alteration without correction of Fe—S enzymes deficit in a mouse model for Friedreich ataxia. Hum Mol Genet. 13, 1017 (May 15, 2004).

H. Seznec, D. Simon, et al. (2004). "Idebenone delays the onset of cardiac functional alteration without correction of Fe—S enzymes deficit in a mouse model for Friedreich ataxia." Hum Mol Genet. 13(10): 1017-1024.

J. Rabinowitz, E., F. Rolling, et al. (2002). "Cross-packaging of a single adeno-associated virus (AAV) type 2 vector genome into multiple AAV serotypes enables transduction with broad specificity." Journal of virology 76(2): 791-801.

R. B. Wilson, Therapeutic Developments in Friedreich Ataxia. J Child Neurol, (Jul. 12, 2012).

R. M. Payne, G. R. Wagner, Cardiomyopathy in Friedreich Ataxia: Clinical Findings and Research. J Child Neurol, (Jul. 4, 2012).

S. Schmucker et al., Mammalian frataxin: an essential function for cellular viability through an interaction with a preformed ISCU/NFS1/ISD11 iron-sulfur assembly complex. PLoS One 6, e 16199 (2011).

Sweeney H L, Feng H S, Yang Z, Watkins H. Proc Natl Acad Sci USA. 1998 Nov. 24; 95(24):14406-10.

V. Campuzano et al., Friedreich's ataxia: autosomal recessive disease caused by an intronic GAA triplet repeat expansion. Science 271, 1423 (1996).

V. Campuzano et al., Frataxin is reduced in Friedreich ataxia patients and is associated with mitochondrial membranes. Hum Mol Genet 6, 1771 (October, 1997).

The invention claimed is:

1. A pharmaceutical composition for treating cardiomyopathy in a Friedreich ataxia patient exhibiting cardiomyopathy, the composition comprising an Adeno-Associated Virus (AAV) vector which comprises a heterologous sequence which consists of a coding sequence encoding FXN or a fragment thereof operably linked to regulatory sequences wherein the fragment comprises a coding sequence encoding amino acids 81-210 of SEQ ID NO:2, wherein said AAV vector is formulated for delivery into myocardium in said patient.

2. The pharmaceutical composition according to claim 1, wherein said FXN comprises the amino acids of SEQ ID NO:2.

3. The pharmaceutical composition according to claim 1, wherein said FXN comprises amino acids 81-210 of SEQ ID NO:2.

4. The pharmaceutical composition according to claim 1 wherein the nucleic acid comprises the nucleic acid sequence of SEQ ID NO:1.

5. The pharmaceutical composition according to claim 1 wherein the nucleic acid comprises a variant of the nucleic acid of SEQ ID NO: 1 which encodes amino acids 81-210 of SEQ ID NO: 2.

6. The pharmaceutical composition according to claim 1 wherein said AAV vector consists essentially of the coding sequence encoding the FXN or the fragment thereof.

7. The pharmaceutical composition according to claim 1 wherein the AAV vector is an AAV1, AAV2, AAV3, AAV4, AA5, AAV6, AAV7, AAV8, AAV9, AAVrh10 vector.

8. The pharmaceutical composition according to claim 7 wherein the AAV vector is the AAVrh10 vector.

9. A method for treating cardiomyopathy in a Friedreich ataxia patient exhibiting cardiomyopathy, comprising directly administering into the heart of said patient a therapeutically effective amount of an AAV vector which comprises a heterologous sequence which consists of a coding sequence encoding frataxin (FXN) or a fragment thereof operably linked to regulatory sequences wherein the fragment comprises a coding sequence encoding amino acids 81-210 of SEQ ID NO:2.

10. The method according to claim 9, wherein said FXN comprises the amino acids of SEQ ID NO:2.

11. The method according to claim 9 wherein said FXN comprises amino acids 81-210 of SEQ ID NO:2.

12. The method according to claim 9 wherein the coding sequence comprises the nucleic acid sequence of SEQ ID NO: 1.

13. The method according to claim 9 wherein the coding sequence encodes the fragment comprising amino acids 81-210 of SEQ ID NO: 2.

14. The method according to claim 9 wherein said AAV vector consists essentially of the coding sequence encoding the FXN or the fragment thereof.

15. The method according to claim 9 wherein the AAV vector is an AAV1, AAV2, AAV3, AAV4, AA5, AAV6, AAV7, AAV8, AAV9, AAVrh10 vector.

16. The method according to claim 15 wherein the AAV vector is the AAVrh10 vector.

17. The method according to claim 9 wherein the AAV vector is administered by intracoronary injection.

18. The method according to claim 9 wherein the AAV vector is administered by intramyocardium injection.

19. The method according to claim 9 wherein the AAV vector is administered by endomyocardiac injection.

20. The method according to claim 9 wherein the AAV vector is administered by epicardiac injection.

21. The method according to claim 9 wherein the AAV vector is administered by intraventricular injection.

* * * * *